United States Patent [19]

Buzas et al.

[11] Patent Number: 4,501,891

[45] Date of Patent: Feb. 26, 1985

[54] METHOD OF FORMING A SOLUTION OF PAPAVRINE CARBANION

[75] Inventors: André Buzas, 25, Rte. de Versailles, 91570 Bievres; Gilbert Lavielle, Orleans, both of France

[73] Assignee: André Buzas, France

[21] Appl. No.: 348,147

[22] Filed: Feb. 11, 1982

Related U.S. Application Data

[63] Continuation-in-part of Ser. No. 169,180, Jul. 15, 1980, abandoned.

[30] Foreign Application Priority Data

Jul. 19, 1979 [GB] United Kingdom ................ 7925275

[51] Int. Cl.³ ............................................. C07D 217/20
[52] U.S. Cl. ...................................... 546/149; 514/307
[58] Field of Search .......................................... 546/149

[56] References Cited

U.S. PATENT DOCUMENTS 1,176,597  3/1916  Picket .................................. 546/149
3,966,724  6/1976  Hughes et al. ...................... 546/149

Primary Examiner—Glennon H. Hollrah
Assistant Examiner—James H. Turnipseed
Attorney, Agent, or Firm—Lucas & Just

[57] ABSTRACT

This invention relates to the new papaverine carbanion of the formula:

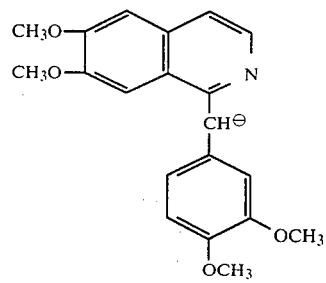

and to a preparation process of the same comprising reacting on papaverine, in a solvent, a slight excess of a highly basic agent.

3 Claims, No Drawings

METHOD OF FORMING A SOLUTION OF PAPAVRINE CARBANION

The present application is a continuation-in-part of prior application Ser. No. 169,180 filed July 15, 1980 and now abandoned in favor of the instant application.

The invention relates to the carbanion of 1-(3,4-dimethoxybenzyl)-6,7-dimethoxy-isoquinoline(papaverine), a compound of ephemeral existence and to the preparation of the same. This compound is interesting because its high reactivity opens up many possibilities for the synthesis of new compounds, particularly those of the formula:

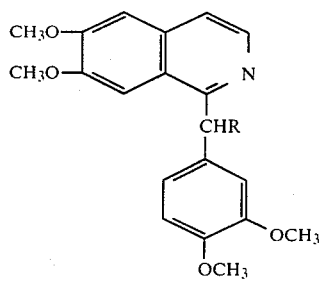

in which R represents a straight chain, branched chain or cyclic, saturated or unsaturated hydrocarbon residue, optionally w-substituted by an alkoxycarbonyl, hydroxy or alkylamino group, or a hydrocarbon chain bonded to the nitrogen atom of the isoquinoline ring to form, with that nitrogen atom and with the 1-C atom of the isoquinoline ring and with the $\alpha$-C atom of the benzyl group, a fused ring structure.

When R stands for a negative charge $\ominus$, the above formula represents the papaverine carbanion. According to this invention, this compound may be prepared by reacting on papaverine, in a basic solvent, a slight excess of a highly basic agent. The preferred highly basic agents are butyl-lithium, a lithium alkyl amide, sodium amide or potassium amide.

The preferred basic solvents are hexamethyl phosphotriamide, tetrahydrofuran, dimethyl formamide or liquid ammonia.

(a) Liquid ammonia/sodamide method

Into a 1 liter three-necked flask provided with stirring means and dry ice refrigeration means are successively introduced 300 ml of liquid ammonia, 0.1 g of ferric chloride acting as catalyst and 0.8 g (0.03 mole) of sodium (cf. Org. Syntheses Coll., Vol. 5, P. 523). The reaction mixture is stirred for 1½ hours and there is then added, in small portions, 10 g (0.0295 mole) of papaverine. To complete the formation of the carbanion, the mixture is stirred for 2 hours. A red solution is obtained, for use as such in synthesis reactions, for instance those described in the examples hereinbelow.

(b) Butyl lithium/hexamethylphosphotriamide method

Into a 1 liter reactor, fitted with heating, cooling and stirring means, are poured 10 g (0.0295 mole) of papaverine and 100 ml of hexamethyl phosphotriamide. Keeping the temperature at approximately 5° C., there is progressively added 18.5 ml (0.03 mole) of commercial butyl lithium in solution in hexane. After the addition is complete, stirring is continued for 1 hour at ambient temperature.

(c) Sodamide/hexamethylphosphotriamide method

Into the same apparatus as in method (b) above are poured 10 g (0.0295 mole) of papaverine and 30 ml of hexamethylphosphotriamide. 1.2 g (0.03 mole) of sodamide are added gently under stirring; the mixture becomes red but there is no evolution of gases. The mixture is heated to 70°–75° C., resulting in evolution of ammonia; stirring is continued for 3 hours until the gaseous evolution ends. The reaction mixture is cooled for use as such in synthesis reactions.

(d) Lithium diisopropylamide/tetrahydrofuran method

In the same apparatus as in method (a) above, cooled by an ethanol/dry ice bath, are poured 400 ml of dry tetrahydrofuran. Lithium diisopropylamide is prepared in situ by adding dropwise at −30° C., 18.5 ml of butyllithium (0.03 mole) dissolved in hexane; 4.2 ml (0.03 mole) of diisopropylamine are added and the mixture is stirred for 15 mn at 10° C.; after cooling at −40° C., 10 g (0.0295 mole) of papaverine (powder) are added and the mixture is stirred for 4 hours at −40° C.

(e) Potassium amide/dimethyl formamide method

In the same apparatus as in example (b) above are poured 10 g (0.0295 mole) of papaverine and 35 ml of dimethyl formamide. 1.7 g (0.03 mole) of potassium amide are slowly added, under stirring. After the end of the addition, stirring is maintained while the reacting mixture is warmed at 70° C. for 3 hours and a half.

The reaction mixture is used as such, after cooling, for further syntheses.

For characterization and identification of the carbanion, the oxidation reaction leading to 1-(3,4-dimethoxybenzoyl)-6,7-dimethoxy-isoquinoline(papaveraldine) is used. Into the solution of the carbanion is bubbled for 2½ hours a current of dry oxygen; then 200 ml of dry toluene is poured in and the ammonia is allowed to evolve in or to evaporate off. The solution is treated at ambient temperature with 200 ml of water and dried m.p. 208° C. (literature: 209°–210° C.).

For further characterization and identification of the carbanion, the following experiments were carried out:

To the solution of carbanion obtained in method (b), maintained at −10° C., are added 4.7 g of methyl iodide (0.05 mol, slight excess) dissolved in 10 ml of hexametapol; the reacting mixture is stirred for one night at room temperature and then poured in 0.5 l of water saturated by ammonium chloride. This mixture is extracted three times by each 75 ml of benzene, dried and evaporated to dryness. By chromatography on silica using as eluent benzene 20/methylene chloride 80, there are obtained 6,3 g of pure product melting at 156° C.

The solution obtained by method (d) is cooled at −30° C. and there are added dropwise 5.45 g of allyl bromide (0.045 mol, slight excess) dissolved in 20 ml of tetrahydrofuran. After stirring one hour at this temperature, the mixture is allowed to reach room temperature and then refluxed for another hour. The resulting mixture is poured in 0.4 l of water saturated by ammonium chloride; after decantation the mixture is extracted three times each with 100 ml of diethyl ether, then dried and evaporated to dryness. By chromatography on silica with eluent benzene 10/methylene chloride 90, there are obtained 7,9 g of pure product melting at 112° C.

The examples which follow describe in detail the syntheses of various compounds starting from the carbanion by way of illustrating the usefulness thereof.

In these examples, the thin layer chromatography (TLC) data was obtained using Merck F 254 plates; the NMR spectra were recorded on Perkin-Elmer R 24 (60 MHz) apparatus; and the I.R. spectra were recorded on Perkin-Elmer 257 apparatus.

EXAMPLE 1

1-(3,4-dimethoxy-phenyl)-butyl)-6,7-dimethoxyisoquinoline

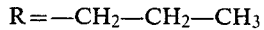
R=—CH$_2$—CH$_2$—CH$_3$

To a solution of the carbanion, obtained by the method (a) above, there is slowly added 5.8 g (0.048 mole) of propyl bromide. After stirring for 1 hour, 200 ml of dry toluene is added and the ammonia is allowed to evaporate off. At ambient temperature, 200 ml of water is added and the reaction mixture is filtered over celite. The toluene solution is then decanted, washed, dried over anhydrous sodium sulfate and concentrated. The oil obtained is chromatographed over a silica gel column (eluent dichloromethane) to give 8,4 g of crystals, m.p. 122° C. Yield 75%.

Of course, this compound may also be obtained from the carbanion obtained by other methods. For instance, by the method of (c) above.

To a solution of the carbanion, obtained by the method (c) 5.8 g (0.048 mole) of propyl bromide are slowly added. After stirring overnight at room temperature, 200 ml of an 10% ammonium chloride aqueous solution are added and the mixture is extracted with benzene (2×100 ml). The benzene solutions were separated, washed with water, dried over anhydrous sodium sulfate and concentrated. The oil obtained is chromatographed over 150 g of silica gel (eluant dichloromethane) to give 6.9 g of crystals, m.p. 122° C.

Yield 60%.

NMR (CDCl$_3$)

δppm: 8.45 (d, 1H, C$\underline{H}$—N═); 7.15 (m, 6H, aromatic protons); 4.65 (t, 1H, C$\underline{H}$—CH$_2$CH$_2$CH$_3$); 3.85 (m, 12H, OCH$_3$); 2.3 (m, 2H, C$\underline{H}$—CH$_2$); 1.3 (m, 2H, —C$\underline{H}$$_2$—CH$_3$); 1 (t, 3H, CH$_2$—C$\underline{H}$$_3$).

EXAMPLE 2

1-[1-(3,4-dimethoxyphenyl)-ethyl]-6,7-dimethoxyisoquinoline

R=—CH$_3$

The title compound is prepared following the methods described in example 1, but using methyl iodide as alkylating agent instead of propyl bromide. The product is obtained in 60% yield by method (a) or 70% yield by method (c) and melts at 156° C.

NMR (CDCl$_3$)

δppm: 8.45 (d, 1H, C$\underline{H}$—N═); 7.15 (m, 6H, aromatic protons); 4.85 (q, 1H, C$\underline{H}$—CH$_3$, J=7 Hz); 3.85 (m, 12H, OCH$_3$); 1.85 (d, 3H, CH—C$\underline{H}$$_3$, J=7 Hz).

EXAMPLE 3

1-[1-(3,4-dimethoxyphenyl)-but-3-enyl]-6,7-dimethoxyisoquinoline

R=—CH$_2$—CH═CH$_2$

Following the method described in example 1, but using allyl bromide as alkylating agent in place of propyl bromide, the title compound (m.p. 112° C.) is obtained in 70% yield.

δppm: 8.40 (d, 1H, C$\underline{H}$—N═); 7.10 (m, 6H, aromatic protons); 5.75 (m, 1H, CH$_2$—C$\underline{H}$═CH$_2$); 5.00 (m, 2H, CH═C$\underline{H}$$_2$); 4.70 (t, 1H, >C$\underline{H}$—CH$_2$—); 3.85 (m, 12H, OCH$_3$); 3.15 (m, 2H, >CH—C$\underline{H}$$_2$—CH═).

EXAMPLE 4

1-[1-(3,4-dimethoxy-phenyl)-heptyl]-6,7-dimethoxy-isoquinoline

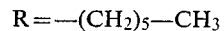
R=—(CH$_2$)$_5$—CH$_3$

Operating as in example 1, but substituting n-hexyl iodide for the propyl bromide, the title compound (m.p. 110° C.) is obtained in 60% yield.

EXAMPLE 5

1-[1-(3,4-dimethoxy-phenyl)-3-ethoxycarbonyl-propyl]-6,7-dimethoxy-isoquinoline

R=—CH$_2$—CH$_2$—COOC$_2$H$_5$

Using ethyl ω-bromo-propionate in place of propyl bromide, but otherwise following the method described in example 1, gives the title compound in 70% yield m.p. 115° C.

NMR (CCl$_4$)

δppm: 8.20 (d, 1H, C$\underline{H}$—N═); 6.9 (m, 6H, aromatic protons); 4.65 (t, 1H, C$\underline{H}$—CH$_2$); 4 (q, 2H, OC$\underline{H}$$_2$—CH$_3$); 3.75 (m, 12H, OC$\underline{H}$$_3$); 2.4 (m, 4H,

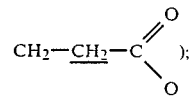

1.2 (t, 3H, OCH$_2$—C$\underline{H}$$_3$).

IR (KBr)

νcm$^{-1}$:

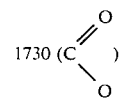

EXAMPLE 6

1-[(1-(3,4-dimethoxy-phenyl)-4-hydroxy-butyl]-6,7-dimethoxy-isoquinoline

R=—(CH$_2$)$_3$—OH 4.4 g (0.01 mole) of 1-[1-(3,4-dimethoxy-phenyl-but-3-enyl]-6,7-dimethoxy-isoquinoline, prepared as described in example 3, are refluxed for 2 hours in a suspension of 2 g of lithium aluminium hybride in tetrahydrofuran. Water is added to hydrolyse any excess reducing agent, and the water/alcohol mixture is then extracted with dichloromethane. The extracts are dried and the dichloromethane is evaporated off to give 3.5 g (yield 90%) of product, melting at 115° C.

IR (KBr)

νcm$^{-1}$: 3350 (OH)

NMR (CDCl$_3$)

δppm: 8.30 (d, 1H, C$\underline{H}$—N═); 7.05 (m, 6H, aromatic protons); 4.6 (t, 1H, C$\underline{H}$); 3.8 (m, 12H, OCH$_3$); 3.6 (m, 2H, C$\underline{H}$$_2$—OH); 2.75 (1H, O$\underline{H}$); 2.35 (m, 2H, CH$_2$—C$\underline{H}$$_2$—CH$_2$); 1.65 (m, 2H, CH—C$\underline{H}$$_2$).

EXAMPLE 7

1-[1-(3,4-dimethoxy-phenyl)-3-hydroxy-propyl]-6,7-dimethoxy-isoquinoline

R=—CH₂—CH₂—OH

This compound is obtained by the following sequence of reactions:

A. Formation of the acetal intermediate:
1-[1-(3,4-dimethoxyphenyl)-3,3-diethoxy-propyl]-6,7-dimethoxy-isoquinoline To a solution containing 0.016 mole of the carbanion obtained by one of the methods described above these is slowly added 5.3 g (0.025 mole) of 2,2-diethoxy-ethyl bromide. After stirring for 1 hour, 200 ml of dry toluene is added and the ammonia is allowed to evaporate off. At ambient temperature, 200 ml of water is added and the whole is filtered over celite. The toluene solution is then decanted, washed, dried over anhydrous sodium sulfate and concentrated. The oil obtained (9.5 g) is hydrolysed without purification.

NMR (CCl₄)

δppm: 8.20 (d, 1H, C$\underline{H}$—N=); 7 (m, 6H, aromatic protons); 4.25 (t, 1H, C$\underline{H}$—CH₂); 3.75 (m, 12H, OCH₃);

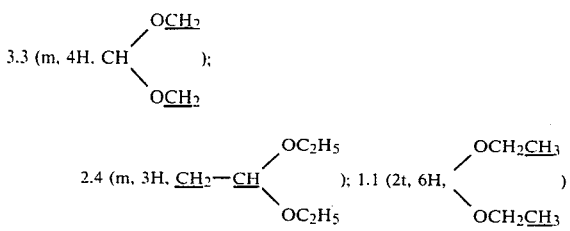

B. Formation of the aldehyde:
[1-1-(3,4-dimethoxy-phenyl)-3-oxo-propyl]-6,7-dimethoxy-isoquinoline 8.7 g (0.014 mole) of the compound prepared in A above are hydrolysed for 2 hours at 50° C. in 200 ml of 2% hydrochloric acid solution. After storing alkalinisation, with Na₂CO₃, the mixture is extracted 3 times by 50 ml of dichloromethane. 7.25 g of an oil are obtained: Yield 95%.

IR

νcm⁻¹: 2730, 1715 (CH=O)

NMR (CDCl₃)

δppm: 9.6 (s, 1H, C$\underline{H}$=O); 8.35 (d, 1H, CH—N=); 7 (m, 6H, aromatic protons); 5.25 (t, 1H, C$\underline{H}$); 3.8 (m, 12H, OCH₃); 2.9

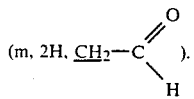

C. Reduction of the aldehyde 3.8 g (0.01 mole) of the compound prepared in B above are reduced by 1 g of sodium borohydride in 40 ml of methanol. After the evaporation off of the solvent, water is added to hydrolyse any excess of the reducing agent and the whole is extracted with dichloromethane. The extracts are dried and the solvent evaporated off to give 3.4 g (yield 90%) of the product in a white meringue like form.

IR

νcm⁻¹: 3250 (OH)

NMR (CDCl₃)

δppm: 8.3 (d, 1H, C$\underline{H}$—N=); 7.05 (m, 6H, aromatic protons); 5 (t, 1H, C$\underline{H}$—CH₂); 3.8 (m, 12H, OCH₃); 3.6 (m, 3H, C$\underline{H}_2$—OH); 2.55 (m, 2H, C$\underline{H}_2$—CH₂).

EXAMPLE 8

1-[1-(3,4-dimethoxy-phenyl)-3-(1-methyl-propylamino)-propyl]-6,7-dimethoxy-isoquinoline

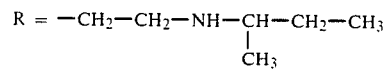

13 g of the aldehyde obtained as described in example 7B above, 2.5 g of 1-methyl-propylamine and 120 ml of ethanol are stirred for 30 minutes over 1 g of molecular sieve at ambient temperature. The mixture is cooled to 0° C. and 3 g of sodium borohydride is added. The mixture is stirred overnight at ambient temperature and worked-up as described in example 7C to give 11.2 g of a yellow oil. This is dissolved in 100 ml of isopropanol and 25.4 ml of 1N hydrochloric acid (1 equivalent) are added to form the hydrochloride. The hydrochloride solution is concentrated to dryness and the residue is taken up in isopropanol and recrystallized therefrom to give 6.3 g of product, m.p. 246° C.

TLC (methanol/acetone/hydrochloric acid 90/10/4)
Rf=0.5 1 spot

NMR (base) (CDCl₃)

δppm: 8.45 (d, 1H, =C$\underline{H}$—N=); 7.3-7.5 (m, 2H, aromatic protons); 6.15-7 (m, 4H, aromatic protons); 4.85 (m, 1H, >C$\underline{H}$—CH₂); 3.95 (s, 6H, OCH₃); 3.75 (s, 6H, OCH₃); 2.1-3 (m, 5H); 1.1-1.6 (m, 3H of which 1H is exchangeable N$\underline{H}$); 0.7-1 (m, 6H).

EXAMPLE 9

1-(3,4-dimethoxy-phenyl)-1,2,3,4-tetrahydro-9,10-dimethoxybenzo(a)quinolizinium chloride R=—(CH₂)₃-terminating on the isoquinoline nitrogen atom The carbanion is treated with 1-bromo-3-iodopropane following the method described in example 1. The oil obtained is refluxed in acetone and the quaternary ammonium salt is isolated in 80% yield. m.p. 220° C.

| Elemental analysis | | C₂₃H₂₆NO₄Cl.H₂O (433.5) | | | | | |
|---|---|---|---|---|---|---|---|
| Calc. | | C % | 63.6 | H % | 6.46 | N % | 3.23 |
| Found | | | 62.9 | | 6.43 | | 2.93 |

EXAMPLE 10

1-(3',4'-dimethoxy-phenyl)-pyrrolo[2,1a]-8,9-dimethoxy-isoquinoline

R=—CH=CH-terminating on the isoquinoline nitrogen atom 7 g (0.0154 mole) of 1-[1-(3,4-dimethoxy-phenyl)-3,3-diethoxy-propyl]-6,7-dimethoxy-isoquinoline, prepared as described in example 7A, are refluxed at 160° C. for 16 hours in a mixture of 9 ml of dimethylformamide, 1.3 ml of 85% formic acid and 0.5 ml concentrated hydrochloric acid. After the reaction mixture has been concentrated under reduced pressure, it is made alkaline and extracted with benzene. 4 g of the title product are obtained, equivalent to a yield of 71.5%. m.p. 170° C.

NMR (CDCl$_3$)

δppm: 6.30–7.50 (m, 9H, aromatic protons); 3.40–3.80 (m, 12H, OCH$_3$).

| Elemental analysis | | | C$_{22}$H$_{21}$NO$_4$ (364) | | | |
|---|---|---|---|---|---|---|
| Calc. | C % | 72.7 | H % | 5.78 | N % | 3.85 |
| Found | | 72.60 | | 5.97 | | 3.82 |

The foregoing are illustrative examples of use of the carbanion of the present invention. Further illustrative examples may be found in applicants' co-pending application Ser. No. 169,164 dated July 15, 1980, now abandoned and incorporated herein by reference. Of particular interest in said co-pending application are the pharmacological studies appearing on pages 13 et seq.

The copending application Ser. No. 169,164 relates to derivatives of isoquinolines. The carbanion of the present invention is used for the preparation of various isoquinolines including the 1-[1-(3,4-dimethoxyphenyl)-3-(1-methyl-propylamino)-propyl]-6,7-dimethoxy-isoquinoline of Example 8 hereinabove. Ser. No. 169,164 discloses that the compounds have therapeutic properties, particularly in the cardiac and vascular fields.

What is claimed is:

1. A method of forming a solution having papaverine carbanion, said method consisting essentially of reacting, in a solvent, papaverine with an agent selected from the group consisting of butyl-lithium, a lithium alkyl amide, sodium amide and potassium amide.

2. Process according to claim 1 wherein the solvent is hexamethyl phosphotriamide, tetrahydrofuran, dimethyl formamide or liquid ammonia.

3. A method of forming a solution having papaverine carbanion, said method consisting essentially of reacting, in a solvent, papaverine with a highly basic agent.

* * * * *